United States Patent
Lui et al.

(10) Patent No.: US 8,766,008 B2
(45) Date of Patent: Jul. 1, 2014

(54) PROCESS FOR PREPARING 2,2-DIFLUOROETHYLAMINE FROM 2,2-DIFLUORO-1-CHLOROETHANE AND AMMONIA

(75) Inventors: Norbert Lui, Odenthal (DE); Rafael Warsitz, Essen (DE); Christian Funke, Leichlingen (DE); Christian Severins, Köln (DE)

(73) Assignee: Bayer Cropscience AG, Monheim (DE)

( * ) Notice: Subject to any disclaimer, the term of this patent is extended or adjusted under 35 U.S.C. 154(b) by 298 days.

(21) Appl. No.: 13/348,484

(22) Filed: Jan. 11, 2012

(65) Prior Publication Data

US 2012/0184777 A1    Jul. 19, 2012

Related U.S. Application Data

(60) Provisional application No. 61/438,679, filed on Feb. 2, 2011.

(30) Foreign Application Priority Data

Jan. 13, 2011 (EP) ..................................... 11150885

(51) Int. Cl.
*C07C 209/06* (2006.01)

(52) U.S. Cl.
USPC ........... 564/386; 564/395; 564/404; 564/407; 564/481

(58) Field of Classification Search
USPC ........................ 564/481, 386, 395, 404, 407
See application file for complete search history.

(56) References Cited

U.S. PATENT DOCUMENTS

| | | | |
|---|---|---|---|
| 4,030,994 A | | 6/1977 | Kollonitsch |
| 5,071,634 A | * | 12/1991 | Maunula et al. ............ 423/588 |
| 6,419,892 B1 | * | 7/2002 | Schutte et al. ............ 423/588 |
| 6,506,361 B1 | * | 1/2003 | Machado et al. ............ 423/659 |
| 7,285,698 B2 | * | 10/2007 | Liu et al. ............ 585/721 |
| 8,188,319 B2 | * | 5/2012 | Lui et al. ............ 564/481 |
| 8,466,293 B2 | * | 6/2013 | Lui et al. ............ 546/329 |
| 2011/0060167 A1 | | 3/2011 | Lui et al. |

FOREIGN PATENT DOCUMENTS

WO    2011/012243    2/2011

OTHER PUBLICATIONS

Swarts, "Ueber Einige Flourhaltige Alkylamine, " Chem Zentralblatt, vol. 75, pp. 944-945, (1904).
Dickey et al., "Flourinated Aminoanthraquinone Dyes," Industrial and Engineering Chemistry, vol. 48, 2, pp. 209-213, (Feb. 1956).
Kluger et al., "Carboxylic Acid Participation in Amide Hydrolysis. Evidence That Separation of a Nonbonded Complex Can Be Rate Determining," J.Am. Chem. Soc., vol. 104, pp. 2891-2897, (1982).
Verniest et al., "Synthesis and Reactivity of 1-Substituted 2-Fluoro- and 2,2-Difluoroaziridines," J. Org. Chem. vol. 72, pp. 8569-8572, (2007).
Hudlicky, "Chemistry of Organic Flourine Compounds," vol. 2, pp. 489-495, (1976).
Houben-Weyl, b. synthesis of flourinated compounds, vol. E 10b/2, pp. 92-98, (2007).
European Search Report for EP-11150885 (Apr. 19, 2011).

\* cited by examiner

*Primary Examiner* — Fereydoun G Sajjadi
*Assistant Examiner* — Pancham Bakshi
(74) *Attorney, Agent, or Firm* — Miles & Stockbridge, P.C.

(57) ABSTRACT

Process for preparing 2,2-difluoroethylamine, comprising the following steps:
  (i) mixing 2,2-difluoro-1-chloroethane and gaseous, liquid or supercritical ammonia in a pressure-stable, closed reaction vessel under a pressure in the range from 10 to 180 bar;
  (ii) reacting the reaction mixture at a reaction temperature in the range from 80° C. to 200° C.;
  (iii) letting down the reaction mixture and isolating 2,2-difluoroethylamine.

19 Claims, No Drawings

PROCESS FOR PREPARING 2,2-DIFLUOROETHYLAMINE FROM 2,2-DIFLUORO-1-CHLOROETHANE AND AMMONIA

CROSS REFERENCE TO RELATED APPLICATIONS

This application claims priority to European Patent Application No. 11150885.9, filed Jan. 13, 2011, and U.S. Provisional Application No. 61/438,679, filed Feb. 2, 2011, the content of both of which are incorporated herein by reference in their entireties.

BACKGROUND

1. Field of the Invention

The present invention relates to a process for preparing 2,2-difluoroethylamine, starting from 2,2-difluoro-1-chloroethane and ammonia.

2. Description of Related Art 2,2-Difluoroethylamine is an important intermediate compound in the preparation of active ingredients. The preparation of 2,2-difluoroethylamine (and also tetrafluoroethylamine) using a halo-2,2-difluoroethane compound, namely bromine-2,2-difluoroethane, was described for the first time in 1904 by Swarts in an article with the title "Über einige fluorhaltige Alkylamine" [Concerning a number of fluorine-containing alkylamines] (Chem. Zentralblatt, Volume 75, 1904, pages 944-945). Swarts uses 1-bromo-2,2-difluoroethane and heats it for 3 days in a tube with 2 mol of alcoholic ammonia at 125-145° C. Swarts describes the full conversion of the starting compound into the compounds difluoroethylamine and tetrafluoroethylamine. It is apparent from the article that 2,2-difluoroethylamine is not prepared selectively, since the reaction equally produced tetrafluoroethylamine, which has to be removed. Both products were isolated by fractional distillation or by their conversion into hydrochlorides or oxalates.

More than 50 years later, in fact in 1956, Dickey et al. in Industrial and Engineering Chemistry 1956, No. 2, 209-213, published a process for preparing 2,2-difluoroethylamine that starts from 2,2-difluoro-1-chloroethane and 28% strength ammonium hydroxide, i.e. 28% strength aqueous ammonia solution. The reactants are reacted in a rocking autoclave. The reaction mixture is heated at temperatures of 135° C. to 140° C. for 31 hours. After the end of the reaction, the reaction mixture is filtered and the amine is removed from the reaction mixture by distillation. However, since there is still a quantity of ammonia and some water in the distillate, the amine is dried over sodium hydroxide and distilled again.

The processes published up to 1956 have the disadvantage that they are not selective, take a very long time, and have a fairly low yield. Aqueous ammonia in combination with the chloride and fluoride ions present in the reaction mixture, and in combination with the high temperatures used in the reactions, is highly corrosive and attacks metallic materials. The processes are therefore not suitable for preparing the desired 2,2-difluoroethylamine in sufficient quantity with cost-effective and environmentally friendly use of resources (e.g. energy and starting materials).

Since that time, no further processes have been published which prepare 2,2-difluoroethylamine using a halo-2,2-difluoroethane compound, particularly 2,2-difluoro-1-chloroethane, and ammonia.

The international patent publication WO2011/012243 (filed as PCT/EP2010/004434) for the first time again described a process for preparing 2,2-difluoroethylamine that starts from 2,2-difluoro-1-haloethane, preferably 2,2-difluoro-1-chloroethane, and ammonia. The process is carried out in the presence of a solvent, and the solvent must not exceed a water content of 15% by volume. The solvent is used in the reaction in an amount of 1 to 50 times, preference being given to an amount of 2 to 20 times. Although the process described in the patent application has distinct advantages over the processes described in 1904 and in 1956, this process is in need of improvement particularly in respect of the environmentally friendly use of resources.

On the basis of the published and unpublished processes for preparing 2,2-difluoroethylamine, the problem now confronted is that of developing a process which starts from 2,2-difluoro-1-chloroethane and ammonia and which avoids the disadvantages identified above.

SUMMARY

It has surprisingly been found that 2,2-difluoro-1-chloroethane and ammonia ($NH_3$) undergo selective reaction to give 2,2-difluoroethylamine even when no solvent is present. Likewise, methods have been found for carrying out the reaction continuously or in part batchwise. A continuous or in part batch process is particularly advantageous in the context of the industrial preparation of 2,2-difluoroethylamine.

The invention accordingly provides a process for preparing 2,2-difluoroethylamine in pure form, i.e. without solvent, which comprises reacting 2,2-difluoro-1-chloroethane with ammonia. The reaction may optionally take place in the presence of a catalyst that accelerates the reaction with ammonia. The process may further encompass a purification step.

The application relates, accordingly, to a process for preparing 2,2-difluoroethylamine, comprising the following steps:
(i) mixing 2,2-difluoro-1-chloroethane and gaseous, liquid or supercritical ammonia in a pressure-stable, closed reaction vessel under a pressure in the range from 10 to 180 bar; preferably under a pressure in the range from 30 bar to 155 bar;
(ii) reacting the reaction mixture at a reaction temperature in the range from 80° C. to 200° C.; preferably at a reaction temperature in the range from 100° C. to 170° C.;
(iii) letting down the reaction mixture and isolating 2,2-difluoroethylamine.

DETAILED DESCRIPTION OF A PREFERRED EMBODIMENT

In the process according to the invention solvents are omitted/not used.

In one embodiment [A] the application relates to a process as defined above in which a catalyst is additionally present in step (i). The catalyst is preferably selected from the following group consisting of alkali metal bromides, alkali metal iodides, ammonium bromide, ammonium iodide, tetraalkylammonium bromides, tetraalkylammonium iodides, tetraalkylphosphoniumhalides, tetraarylphosphonium halides, tetrakis(dimethylamino)phosphonium bromide, tetrakis(diethylamino)phosphonium bromide, tetrakis(dipropylamino)phosphonium bromide and tetrakis(dipropylamino)phosphonium chloride, and bis(dimethylamino)[(1,3-dimethylimidazolidin-2-ylidene)amino]methylium bromide. Particularly preferred catalysts are sodium bromide, potassium bromide, sodium iodide, potassium iodide, tetrabutylammonium bromide or tetraphenylphosponium bromide; an especially preferred catalyst is sodium or potassium iodide.

In one embodiment [B], the application relates to a process as defined above or as described in embodiment [A] in which the addition/supply of 2,2-difluoro-1-chloroethane and ammonia in step (i) takes place continuously and in which a static mixer is used for the mixing.

In one embodiment [C], the application relates to a process as defined above or as described in embodiment [A] or [B] which is carried out completely continuously.

In one embodiment [D], the application relates to a process as defined in embodiment [C] in which use is made as reaction vessel of a thermally conditionable flow reactor which comprises at least two zones, the first zone comprising a static mixer, and step (i) taking place in this first zone and step (ii) taking place in the second zone (reaction zone). The flow reactor preferably comprises an additional zone at the end of the reaction zone or subsequent to the reaction zone, in which the reaction pressure is reduced.

In one embodiment [E], the application relates to a process as defined in embodiment [D] in which the residence time of 2,2-difluoro-1-chloroethane and ammonia in the second zone, i.e. the reaction zone, is in the range from about 20 seconds to about 400 minutes; preferably in the range from about 1 minute to about 400 minutes; very preferably in the range from about 15 minutes to about 45 minutes.

In one embodiment [F], the application relates to a process as described in embodiment [D] or [E] where measuring instruments or measuring probes are present in the flow reactor, preferably in the reaction zone.

In the process of the invention the molar ratio of 2,2-difluoro-1-chloroethane to the ammonia used is in the range from about 6:1 to about 1:200, preferably in the range from about 4:1 to about 1:150, more preferably in the range from about 1:1 to about 1:100.

The ammonia ($NH_3$) used in the process of the invention may be added in gaseous, liquid (i.e. as condensed $NH_3$ gas) or supercritical state (i.e. above its critical temperature and above its critical pressure) to the 2,2-difluoro-1-chloroethane. The addition of $NH_3$ in step (ii) takes place preferably in gaseous or liquid state.

Suitable catalysts for use in the process of the invention are all those which accelerate the reaction with ammonia. Mixtures of suitable catalysts are also conceivable. Catalysts suitable in accordance with the invention are more particularly alkali metal bromides and iodides (e.g. sodium iodide, potassium iodide, potassium bromide); ammonium bromide and ammonium iodide; tetraalkylammonium bromides and iodides (e.g. tetraethylammonium iodide); certain phosphonium halides, such as tetraalkyl- and tetraarylphosphonium halides (e.g. hexadecyltributylphosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino)phosphonium bromide, tetrakis(diethylamino)phosphonium bromide, tetrakis(dipropylamino)phosphonium chloride and tetrakis(dipropylamino)phosphonium chloride or bromide; and also bis(dimethylamino)[(1,3-dimethylimidazolidin-2-ylidene)amino]methylium bromide.

Preferred catalysts are sodium bromide, potassium bromide, sodium iodide, potassium iodide, tetrabutylammonium bromide or tetraphenylphosponium bromide, particular preference being given to sodium or potassium iodide.

The catalyst may also be generated in situ. As for example by means of a reaction of HBr or HI with ammonia. Furthermore, the catalyst may also be generated in-situ by addition of highly reactive alkyl bromides or iodides (e.g. methyl or ethyl bromide or iodide).

In the process of the invention the catalyst, if present, is used in a concentration of around 0.01% to around 25% by weight, based on the 2,2-difluoro-1-chloroethane used. Higher concentrations are possible in principle. The catalyst is used preferably at a concentration of around 0.2% to around 25% by weight, more preferably of around 0.4% to around 20% by weight, very preferably of around 0.5% to around 15% by weight. Alternatively the catalyst may be used with preference at a concentration of around 0.05% to around 3% by weight, of around 0.1% to around 10% by weight or of around 0.5% to around 10% by weight.

The reaction is carried out in principle under pressure in a pressure-stable, closed reaction vessel (e.g. autoclave, flow reactor or tube reactor). The pressure during the reaction is dependent on the amount of 2,2-difluoro-1-chloroethane, on the amount of ammonia used, on the reaction temperature and, if pumps are used to charge the reaction vessel, on the conveying pressure of the pumps. If a pressure increase is desired, then in the case of the batch process, in addition to increasing the reaction temperature, an additional increase in pressure may be achieved through the introduction of an inert gas, such as nitrogen or argon, for example. In the continuous process, the pressure can be changed via the pump performance.

The mixing of the two reactants is done under a pressure which ought to be situated in the range from about 10 to about 180 bar, preferably in the range from 30 to 155 bar, the temperature at which the reactants are mixed being variable and being situated commonly in the range from room temperature (about 20° C.) to about 180° C. The reaction according to the invention can be carried out within a wide temperature range (e.g. in the range from about 80° C. to about 200° C.). The reaction is carried out preferably in a temperature range from about 100° C. to about 170° C.

The inventors have ascertained that as a result of operation in bulk, i.e. without addition of a solvent, the reaction vessel used (in this case the autoclave or the flow reactor) corrodes only very little, in spite of the high reaction pressure and in spite of the relatively high reaction temperature, with the consequence that the process can be carried out on an industrial scale.

The inventors have likewise ascertained that the desired 2,2-difluoroethylamine is obtained, by the process of the invention, with good yields, in short reaction times and in high purity, which means that extensive working-up of the direct reaction product is generally unnecessary. All this is surprising in view of the fact that it is known, from M. Hudlicky, Chemistry of Organofluorine Compounds, 2nd Edition, 1976, p. 489-490 and from Houben Weyl, E 10b/2, pp. 92-98, that basic conditions favour preferential formation of vinylidene fluoride, which may form from 2,2-difluorochloroethane with elimination of HCl. It is also known from J. Org. Chem. 2007, 72 (22) 8569 that 2,2-difluoroethylamine is highly reactive and may undergo further reaction under the reaction conditions of the invention.

The process of the invention may be carried out both entirely continuously and entirely batchwise. Likewise, in the process of the invention performed batchwise, certain reaction steps may be carried out continuously. Processes of this kind are referred to as "in part batch" processes.

By continuous processes or steps are meant, here, those in which the feeding of the reactants into a reaction vessel (e.g. flow reactor) and the discharge of the products from the reaction vessel take place at the same time but at separate locations. Batch processes or steps are understood here to be those which proceed in temporal succession—for example, feeding of the reactants into a reaction vessel, then reaction of the reactants, followed by discharge of the products from the reaction vessel. The continuous process is suitable more particularly for preparing large quantities.

The reaction time for the process of the invention carried out in part or completely batchwise is in the range from about 0.5 hour to about 16 hours. A longer reaction time is possible in principle.

It is preferred to carry out the adding and the mixing of step (i) in the process of the invention continuously, using a static mixer.

In the process of the invention carried out continuously, operation takes place in a flow reactor. The flow reactor is preferably thermally conditionable. A flow reactor suitable in accordance with the invention comprises at least two zones, of which at least one of the zones is thermally conditionable. In the first zone, the reactants, namely 2,2-difluoro-1-chloroethane and $NH_3$, are mixed. If a catalyst is used in the reaction according to the invention, then it may be introduced into the reaction vessel together with one of the reactants, more particularly 2,2-difluoro-1-chloroethane. Advantageously there is a static mixer installed in the first zone. The second, thermally conditionable zone, referred to as the residence zone or reaction zone, is where the reaction takes place. At the end of the reaction zone, the reaction pressure is reduced, causing dissolved $NH_3$ to undergo partial or complete evaporation. Through the reduction in pressure, the organic and/or inorganic salts that have formed during the reaction undergo partial or complete crystallization. Liquid 2,2-difluoroethylamine can then be isolated and collected.

The desired residence times in the residence zone or reaction zone, and the reaction conversions to be achieved, are dependent primarily on the metering rate of all of the reactants, including any catalysts present (reaction mixture), and on the flow rate of the reaction mixture through the residence section (length of the reaction zone). The general rule is that the length of the residence time is dependent on the reaction temperature: the higher the reaction temperature, the shorter the residence time ought to be. Generally speaking, the residence times of the reaction mixture in the reaction zone are in the range from about 20 seconds (sec) to about 400 minutes (min), preferably in the range from about 1 min to about 400 min, very preferably in the range from about 15 min to about 45 min.

Consideration may be given to supplying the reaction mixture with $NH_3$ along the whole residence section or along part of the residence section.

The residence time of the reaction mixture in the reaction zone is normally controlled by the flow rate through the reaction zone and by the volume of the reaction zone. It is advantageous if the course of the reaction is monitored using measuring instruments, such as, for example, temperature meters, viscometers, thermal conductivity meters or refractometers, or instruments or probes for measuring infrared and/or near-infrared spectra. The measuring instruments must of course be suitable for flowing media, and can be integrated in the flow reactor.

Static mixers are generally tubes or channels with fixed internals which utilize the flow energy to bring about the mixing of fluid product streams. A conveying unit (e.g. a pump) forces the liquid, for example, through the tube provided with fixed (i.e. static) mixer internals. Here, the fluid product streams which follow the axis of principal flow are divided into component streams, which then, depending on the nature of the internals, are swirled with one another and mixed.

As compared with mixers containing moving stirring elements, static mixers have an often smaller chamber volume and a very low energy consumption. Static mixers are closed systems requiring neither maintenance nor inertization. With static mixers, it is the flow energy of the fluid product streams that is exploited, whereas with dynamic mixers (e.g. stirrers) the mixing or homogenization of the fluid product steams to be mixed is achieved by means of moving elements.

An overview of various types of static mixer of the kind used in conventional process engineering is given by, for example, the article "Statische Mischer and ihre Anwendungen" [Static mixers and their applications] by M. H. Pahl and E. Muschelknautz, in Chem.-Ing.-Techn. 52 (1980) No. 4, pp. 285-291. That article and the static mixers described therein are hereby incorporated by reference. Static mixers are described in U.S. Pat. No. 4,062,524 B, for example, and are available commercially under the trade name "Sulzer SMX®" mixers. The aforementioned mixers are composed of two or more grids which are perpendicular to one another and are composed of parallel strips which are connected to one another at their intersections and are set at an angle with respect to the principal flow direction of the fluid product streams to be mixed, so as to divide the product streams into component streams and to mix them as described above. Since mixing takes place only along a preferential direction transverse to the principal flow direction, it is necessary for a plurality of mixer internals, rotated by 90° relative to one another, to be disposed one after another.

After reaction has taken place in the continuous, in part batch or batch process, the reaction mixture is preferably worked up and the desired 2,2-difluoroethylamine is isolated and, if necessary, purified. Accordingly, step (iii) of the process of the invention comprises letting down the mixture, i.e. causing the pressure prevailing in the reaction vessel to subside, and removing the catalyst, if present, and the organic and/or inorganic salts formed during the reaction. Isolation is effected advantageously by filtration of the reaction mixture and fractional distillation of the 2,2-difluoroethylamine.

By varying the reaction pressure it is possible to bring about partial or complete crystallization of organic and/or inorganic salts that have formed during the reaction, an example being ammonium chloride. The letdown produces partial or complete removal of ammonia which has not been consumed and is still in solution.

The isolating of 2,2-difluoroethylamine takes place by known methods, specifically extraction, (fractional) distillation, chromatography—the methods can be combined. The isolating or purifying of a 2,2-difluoroethylamine salt, such as salts of organic or inorganic acids (e.g. hydrochlorides or acetates), for example, is accomplished preferably by crystallization. Examples of salts of 2,2-difluoroethylamine include the 2,2-difluoroethylamine hydrochloride and 2,2-difluoroethylamine acetate. Water-soluble salts can be purified by extraction of the aqueous solutions. The amine can then, finally, be released from its salts by reaction with organic or inorganic bases. Preferred bases are $NaHCO_3$, $Na_2CO_3$ or NaOH.

The present invention is illustrated using the examples below, but the invention is not confined to these examples.

PREPARATION EXAMPLES FOR THE REACTION OF 2,2-difluoro-1-chloroethane AND AMMONIA

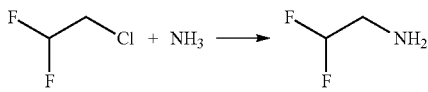

Example 1

Batch Process

An amount of 215 g (2.10 mol) of 2,2-difluoro-1-chloroethane and 2.38 g of potassium bromide are charged to an autoclave and admixed with 136 g of ammonia (anhydrous). The molar ratio of 2,2-difluoro-1-chloroethane to ammonia is 1:4. The reaction mixture is heated to 140-145° C. and stirred at this temperature for 9 hours. In the course of the reaction, the pressure falls from about 50 bar to about 35 bar. The reaction mixture is cooled to 0° C. and let down over the course of 1 hour. It is admixed with 400 g of N-methylpyrrolidone (NMP) and water until all the salts are in solution. According to quantitative GC analysis (external standard), a chemical yield of 59% of 2,2-difluoroethylamine is obtained, based on 2,2-difluoro-1-chloroethane introduced.

Example 2

Continuous Process Using a Flow Reactor

A quantity of 2,2-difluoro-1-chloroethane (98% product) was introduced into a receiver 1. Receiver 1 is connected to a high-pressure pump. An ammonia gas bottle with anhydrous $NH_3$ was connected as receiver 2 to another high-pressure pump. The two receivers were connected by a preliminary thermal conditioning section (room temperature) with a static mixer, having a volume of 10 ml (mixing zone), and connected to the outlet duct of this section was a thermally conditionable residence element with a volume of 57.2 cm$^3$ (reaction zone) and a surface area-to-volume ratio of 18 cm$^2$/cm$^3$ (at 155° C.). Mounted at the exit of the residence section was a pneumatically regulated Kämmer valve. The Kämmer valve allowed the pressure in the reactor to be held at a constant 155 bar and at the same time let down into the downstream phase separator. From receiver 1, 2,2-difluoro-1-chloroethane, with a volume flow rate of 0.16 ml/min, and, from receiver 2, ammonia, with a volume flow rate of 1.28 ml/min, were pumped continuously through the reactor. The residence time of the reaction mixture in the mixing zone was 7 minutes and the residence time in the reaction zone was 40 minutes. The reaction was monitored by HPLC.

Downstream of the Kämmer valve, the product stream was let down into a phase separator, where $NH_4Cl$ formed by the reaction underwent crystallization. Following phase separation and filtration, 2,2-difluoroethylamine was collected. After a quantitative gas chromatographic analysis (external standard) 2,2-difluoroethylamine was obtained in a yield of 60-70% (calculated on the amount of 2,2-difluoro-1-chloroethane employed).

$^1$H NMR (CDCl$_3$): 5.5-5.9 (m, 1H), 2.94-3.1 (m, 2 H), 1.26 (br m, NH$_2$)

The invention claimed is:

1. A process for preparing 2,2-difluoroethylamine, comprising:
   (i) mixing 2,2-difluoro-1-chloroethane and gaseous, liquid or supercritical ammonia to form a reaction mixture in a pressure-stable, closed reaction vessel under a pressure of from 10 to 180 bar;
   (ii) reacting the reaction mixture at a reaction temperature of from 80° C. to 200° C.;
   (iii) letting down the reaction mixture and isolating 2,2-difluoroethylamine,
   wherein the process is performed without any solvent.

2. The process according to claim 1, wherein a catalyst is present in (i), and said catalyst comprises at least one selected from the group consisting of alkali metal bromides, alkali metal iodides, ammonium bromide, ammonium iodide, tetraalkylammonium bromides, tetraalkylammonium iodides, tetraalkylphosphoniumhalides, tetraarylphosphonium halides, tetrakis(dimethylamino)phosphonium bromide, tetrakis(diethylamino)phosphonium bromide, tetrakis(dipropylamino)phosphonium bromide and tetrakis(dipropylamino) phosphonium chloride, and bis(dimethylamino)[(1,3-dimethylimidazolidin-2-ylidene)amino]methylium bromide.

3. The process according to claim 1, wherein in (i), the mixing of 2,2-difluoro-1-chloroethane and ammonia takes place continuously and a static mixer is used for the mixing.

4. The process according to claim 1, carried out completely continuously.

5. The process according to claim 4, wherein said process employs a thermally conditionable flow reactor as a reaction vessel, and wherein said reaction vessel comprises at least two zones, the first zone comprising a static mixer, and wherein (i) takes place in said first zone and (ii) takes place in a second zone which comprises a reaction zone.

6. The process according to claim 4, wherein residence time of 2,2-difluoro-1-chloroethane and ammonia in a second zone optionally comprising the reaction zone is from about 20 seconds to about 400 minutes.

7. The process according to claim 5, wherein a measuring instrument and/or measuring probe is present in the flow reactor.

8. A process according to claim 5, wherein the flow reactor optionally further comprises an additional zone at an end portion of the reaction zone and/or subsequent to the reaction zone, in which the reaction pressure is reduced.

9. The process according to claim 1, wherein in (i), the mixing of 2,2-difluoro-1-chloroethane and ammonia takes place under a pressure of from 30 bar to 155 bar.

10. The process according to claim 1, wherein in (ii), the reaction mixture is reacted at a reaction temperature of from 100° C. to 170° C.

11. The process according to claim 4, wherein residence time of 2,2-difluoro-1-chloroethane and ammonia in a second zone comprising the reaction zone is from about 15 minutes to about 45 minutes.

12. The process according to claim 1, wherein the molar ratio of 2,2-difluoro-1-chloroethane to the ammonia is in the range from about 6:1 to about 1:200.

13. The process according to claim 1, wherein the molar ratio of 2,2-difluoro-1-chloroethane to the ammonia is in the range from about 1:1 to about 1:100.

14. The process according to claim 1, wherein a catalyst is present in (i), and said catalyst comprises at least one selected from the group consisting of sodium bromide, potassium bromide, sodium iodide, potassium iodide, tetrabutylammonium bromide, and tetraphenylphosponium bromide.

15. The process according to claim 1, wherein a catalyst is present in (i), and said catalyst comprises at least one selected from the group consisting of sodium iodide and potassium iodide.

16. The process according to claim 2, wherein the catalyst is used in a concentration of about 0.01% to about 25% by weight, based on the 2,2-difluoro-1-chlorethane used.

17. The process according to claim 2, wherein the catalyst is used in a concentration of about 0.5% to about 15% by weight, based on the 2,2-difluoro-1-chlorethane used.

18. The process according to claim 8, wherein the additional zone at an end portion of the reaction zone and/or subsequent to the reaction zone, in which the reaction pressure is reduced, is present.

19. The process according to claim 1, wherein a yield of greater than 59% of 2,2-difluoroethylamine is obtained.

* * * * *